United States Patent [19]

Klassen

[11] Patent Number: 5,458,863
[45] Date of Patent: Oct. 17, 1995

[54] COLD PROCESS FOR HYDROXYAPATITE COATINGS

[76] Inventor: Robert D. Klassen, 16 Limeridge Drive, Kingston, Ontario, Canada, K7K 6M3

[21] Appl. No.: 345,607

[22] Filed: Nov. 25, 1994

[51] Int. Cl.$^6$ .................................................. C25D 9/08
[52] U.S. Cl. ....................... 423/307; 423/308; 205/220; 205/318; 204/100
[58] Field of Search .................................. 205/220, 318; 204/180.2, 100; 423/307, 308

[56] References Cited

U.S. PATENT DOCUMENTS 4,335,086  6/1982  Spencer ..................................... 423/308
5,310,464  5/1994  Redepenning ........................ 204/180.2

Primary Examiner—John Niebling
Assistant Examiner—Brendan Mee

[57] ABSTRACT

The invention is a method, involving temperatures between room temperature and 100° C., for coating a metal substrate with hydroxyapatite. The intended application is coating porous metal coats of orthopedic and endosseous implants such that the underlying metal is not sintered and the hydroxyapatite coating has chemical and physical properties that are close to biological apatite. The method involves: (i) cleaning the metal substrate, (ii) coating the metal substrate with brushite by electrodeposition at room temperature, (iii) dislodging bubbles periodically during brushite electrodeposition, and (iv) converting the brushite coating to hydroxyapatite at a temperature between room temperature and 100° C.

7 Claims, No Drawings

1

COLD PROCESS FOR HYDROXYAPATITE COATINGS

CROSS REFERENCE TO RELATED APPLICATIONS Canadian patent File No. 2,125,333 (Jun. 6, 1994)

BACKGROUND OF THE INVENTION

1. FIELD OF THE INVENTION

The invention is a process ,involving temperatures between room temperature and 100° C., for coating a metal substrate with hydroxyapatite.

2. DESCRIPTION OF THE PRIOR ART

One method of fixation for orthopedic and endosseous implants is by bony ingrowth into the pores of a "porous coat" on the metallic surface. Some improvement in this fixation is achieved by plasma-spraying heat-treated hydroxyapatite onto the porous coat of the implant. Hydroxyapatite, containing a small amount of carbonate, is the principal inorganic component of bones and teeth. The high temperature involved in the plasma-spraying process, however, causes physical and chemical modifications of the hydroxyapatite powder and also some sintering of the underlying metal porous coat.

One cold-temperature method is to apply hydroxyapatite to a metal by electrophoresis from a suspension of hydroxyapatite in an organic solvent. The resulting coating, however, significantly loosens and dissolves when exposed to water.

A hybrid cold/hot method is to electrodeposit tricalcium phosphate hydrate and then sinter the coating. This heat treatment, which produces substantial conversion of the coating to hydroxyapatite, also sinters to some degree an underlying porous metal coat.

The point of departure for this invention is a method of electrodepositing brushite from a solution of calcium phosphate monobasic. When a metal with a porous coat is the substrate, however, the brushite crystals are too easily abraded off for application as a coating for an implant. Another limitation is that brushite is not currently permitted as an implant coating.

SUMMARY OF THE INVENTION

The object of this invention is to produce a coating of hydroxyapatite on the porous coat of a metal implant such that sintering of the metal is avoided and the hydroxyapatite coating has chemical and physical properties that are as close to biological hydroxyapatite as possible.

The invention involves two main aspects: (i) combining brushite electrodeposition with a method for converting the brushite coating into hydroxyapatite, and (ii) improving the resistance to abrasion of the hydroxyapatite coating by periodically dislodging bubbles from the metal substrate during brushite electrodeposition.

DESCRIPTION OF THE PREFERRED EMBODIMENTS

Development of a coating of hydroxyapatite onto a porous metal substrate, such as grit-blasted or plasma-sprayed titanium alloy, consists of three main steps: (i) cleaning the metal, (ii) electrodeposition of brushite onto the metal at room temperature, and (iii) conversion of the brushite coating into hydroxyapatite at a temperature between room temperature and 100° C.

The brushite coating, during electrodeposition, will not develop evenly on the metal substrate where there are surface contaminants. An effective method of removing contaminants such as dust and finger-pit residue from a metal substrate is the following set of steps: (i) scrubbing with a brush and an alkaline detergent for several minutes while wearing latex gloves, (ii) immersing in an ultrasonic bath of alkaline detergent for 2 hours, (iii) rinsing with water, and (iv) immersing two or more times in an ultrasonic bath of water (ASTM Grade 1) for 20 minutes. The zone to be coated should not be touched with fingers after starting the scrubbing step. The metal substrate may be dried with a flow of warm air. Zones of the metal substrate where coating is not desired may be taped at this point.

The electrolyte for the brushite electrodeposition step is made by dissolving 9 g of calcium phosphate monobasic per liter of water (ASTM Grade 1). This mixture should be stirred for about 30 minutes and then allowed to clarify for about 12 hours. The pH of the clarified supernatant is about 3.5.

The anode for the electrodepositon step may be constructed by wrapping platinum wire around a frame of polypropylene rod such that the external surface area of the platinum is roughly equal to the surface area of the metal that is to be coated. The polypropylene frame should approximately conform to the shape of the metal substrate such that the distance between the metal substrate is roughly equal and from 1 to 5 cm. The electrical connections to the anode and metal substrate should be arranged such that the only metal parts that are wetted by the electrolyte are the platinum on the anode side and the metal substrate on the cathode side.

The electrodeposition step is best operated in galvanostatic mode. A suitable superficial current density is 2 $mA/cm^2$. As the brushite coating develops the voltage between the anode and cathode rises. The process may be terminated when either the voltage reaches a desired maximum or a desired time of electrodeposition has been reached.

The resistance to abrasion of the brushite coating is improved, particularly with deep surfaces such as a plasma-sprayed porous coat, if the bubbles are periodically dislodged from the metal substrate during brushite electrodeposition. Bubble dislodgment may be accomplished by rapping or jarring the metal substrate sufficiently so that bubbles are released. A suitable period of time between bubble dislodgment is 20 seconds.

After the electrodeposition step, the metal substrate may be removed from the electrolyte and the coating rinsed with de-ionized water and any taping removed. Care must be taken to prevent any object from scraping the coating as it is easily scarred at this stage.

Conversion of the brushite coating to hydroxyapatite is accomplished by immersing the metal substrate into a conversion liquor until the transformation is complete. The conversion liquor is made by adding sufficient potassium hydroxide to water (ASTM Grade 1) so that the pH is about 10. The time required for transforming the brushite coating to hydroxyapatite depends on the temperature of the conversion liquor. For example, at 80° C. conversion is complete within 36 hours. A higher conversion temperature permits a shorter conversion period. The normal boiling point of the conversion liquor is a sensible upper limit for the conversion temperature. This is still cold relative to the temperatures that induce sintering of the metal substrate. The carbonate content of the resulting coating may be increased by adding potassium carbonate to the conversion liquor or decreased by bubbling a $CO_2$-free gas through the conversion liquor.

The resulting coating, based on XRD and FTIR characterizations, is hydroxyapatite that is free of any other calcium phosphate compounds. The crystallinity is about 85% compared to a heat-treated hydroxyapatite. With no attempt to add carbonate ions to the conversion liquor or to exclude carbon dioxide from the conversion liquor, the coating contains a small amount of carbonate.

I claim:

1. A process for coating a metal substrate with hydroxyapatite comprising:
   (a) cleaning the metal substrate and then;
   (b) coating the metal substrate with brushite by electrodeposition;
   (c) periodically dislodging bubbles from the metal substrate during the electrodeposition of brushite and then;
   (d) converting the brushite coating to a hydroxyapatite coating by immersing the metal substrate into an aqueous conversion liquor until the brushite coating is completely converted to a hydroxyapatite coating.

2. A process as claimed in claim 1 comprising cleaning the metal substrate by scrubbing it with a brush and immersing it in an ultrasonic bath.

3. A process as claimed in claim 1, comprising dissolving calcium phosphate monobasic into water and clarifying to prepare an electrolyte for brushite electrodeposition having a pH between 3.0 and 3.7.

4. A process as claimed in claim 1 comprising constructing an anode for brushite electrodeposition by wrapping platinum wire around a frame of polypropylene rod.

5. A process as claimed in claim 1 comprising applying a superficial current density of between 0.5 and 5 $mA/cm^2$ during the brushite electrodeposition.

6. A process as claimed in claim 1 wherein the conversion liquor consists of water and potassium hydroxide, wherein the pH of the conversion liquor is maintained above 7 and wherein the conversion liquor is maintained at a temperature between room temperature and 100° C. until the brushite coating is completely converted to a hydroxyapatite coating.

7. A process as claimed in claim 6 further comprising adding potassium carbonate to increase the concentration of carbonate ions in the conversion liquor thereby increasing the carbonate concentration in the hydroxyapatite coating and/or bubbling $CO_2$-free gas through the conversion liquor to decrease the concentration of carbonate ions in the conversion liquor thereby decreasing the concentration of carbonate in the hydroxyapatite coating.

* * * * *